(12) United States Patent
Gutierrez Montes et al.

(10) Patent No.: US 10,602,741 B2
(45) Date of Patent: Mar. 31, 2020

(54) ORGAN-CHIMERIZATION MAINTENANCE APPARATUS AND METHOD OF USE

(71) Applicant: UNIVERSIDAD DEL VALLE, Cali (CO)

(72) Inventors: Jose Oscar Gutierrez Montes, Cali (CO); Alejandra Maria Jerez Valderrama, Cali (CO); Jaime Alfonso Muñoz Botina, Cali (CO)

(73) Assignee: Universidad del Valle (CO)

( * ) Notice: Subject to any disclaimer, the term of this patent is extended or adjusted under 35 U.S.C. 154(b) by 0 days.

(21) Appl. No.: 15/823,630

(22) Filed: Nov. 28, 2017

(65) Prior Publication Data

US 2018/0146662 A1    May 31, 2018

(30) Foreign Application Priority Data

Nov. 28, 2016 (CO) .......... NC2016/0004700
Dec. 1, 2016 (CO) .......... NC2016/0004900

(51) Int. Cl.
  *A01N 1/02* (2006.01)
(52) U.S. Cl.
  CPC ......... *A01N 1/0247* (2013.01); *A01N 1/0226* (2013.01); *A01N 1/0284* (2013.01)
(58) Field of Classification Search
  CPC ....... A01N 1/02; A01N 1/0247; A01N 1/0273
  USPC .......... 435/1.2, 284.1, 286.6, 289.1
  See application file for complete search history.

(56) References Cited

U.S. PATENT DOCUMENTS

| | | | | |
|---|---|---|---|---|
| 6,046,046 A * | 4/2000 | Hassanein | ............ | A01N 1/0247 435/284.1 |
| 6,899,850 B2 * | 5/2005 | Haywood | ............. | B01F 1/0033 215/306 |
| 7,811,808 B2 * | 10/2010 | van der Plaats | ......... | A01N 1/02 435/1.2 |
| 2004/0224299 A1 * | 11/2004 | Garland | .................... | A01N 1/02 435/1.2 |
| 2005/0153271 A1 * | 7/2005 | Wenrich | .................... | A01N 1/02 435/1.1 |
| 2007/0178018 A1 * | 8/2007 | Virno | .................... | B01L 3/5021 422/400 |
| 2009/0197325 A1 * | 8/2009 | Fishman | .................. | A01N 1/02 435/284.1 |
| 2011/0076666 A1 * | 3/2011 | Brassil | ................. | A01N 1/0247 435/1.2 |
| 2011/0294108 A1 * | 12/2011 | Argoudelis | .......... | A01N 1/0247 435/1.2 |
| 2012/0292320 A1 * | 11/2012 | Judson | ................. | A01N 1/0247 220/212 |

FOREIGN PATENT DOCUMENTS

| | | | | |
|---|---|---|---|---|
| EP | 2179648 A1 * | 4/2010 | .......... | A01N 1/0263 |
| WO | WO-9103934 A1 * | 4/1991 | .............. | A01N 1/02 |

OTHER PUBLICATIONS

Chavatte Arnaud, "English language machine translation of document EP2179648A1". (Year: 2010).*

* cited by examiner

*Primary Examiner* — Liban M Hassan
(74) *Attorney, Agent, or Firm* — The Morales Law Firm; Joseph L. Morales

(57) ABSTRACT

An organ-chimerization maintenance device. The organ-chimerization device includes at least one large cannula connector that connects to at least one of an organ's vessels. The large cannula is configured to supply a chimerization solution to the organ. The organ-chimerization device also includes a an oxygenation cannula connector that facilitates oxygenation of the organ during chimerization.

9 Claims, 7 Drawing Sheets

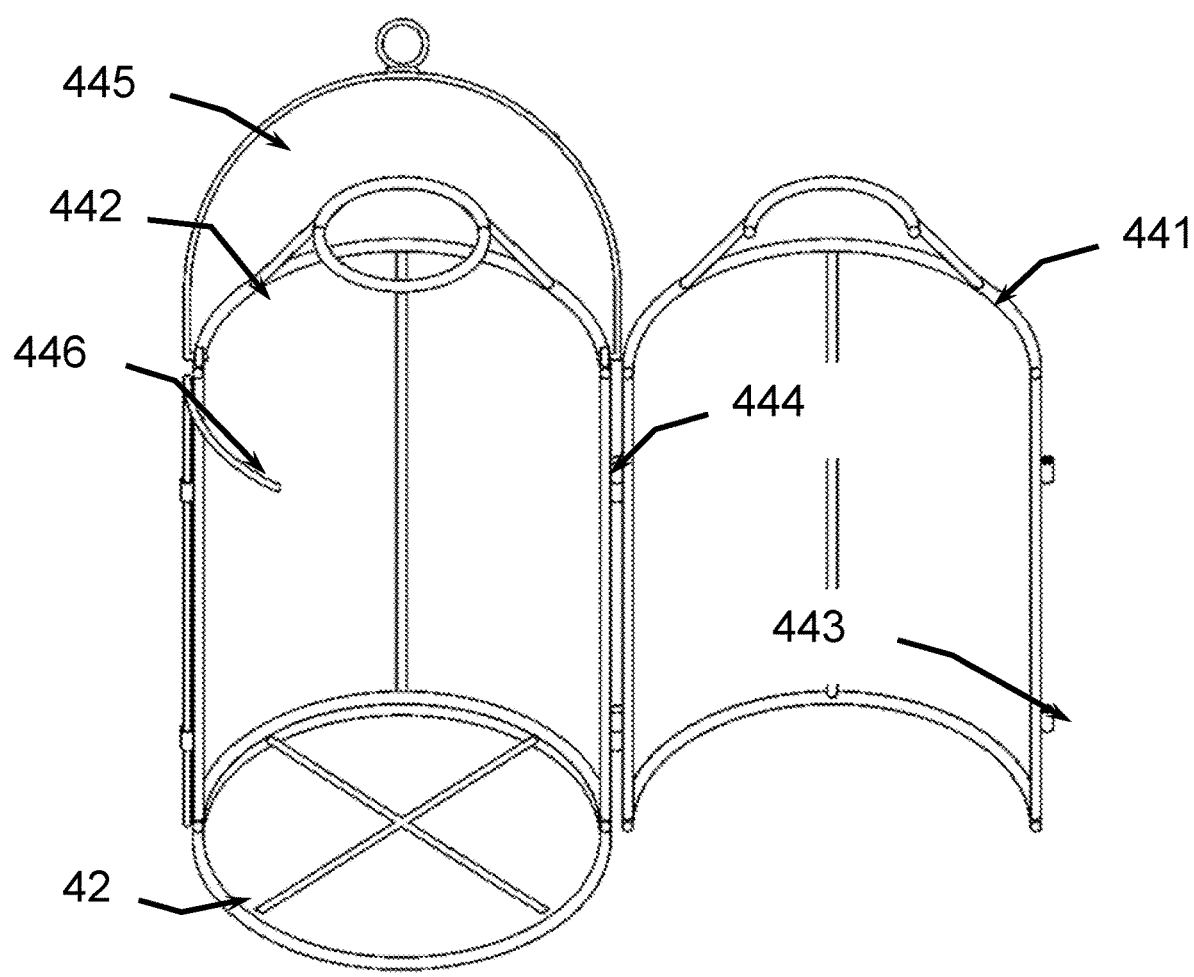

ORGAN-CHIMERIZATION MAINTENANCE APPARATUS AND METHOD OF USE

CROSS-REFERENCE TO RELATED APPLICATIONS

This application claims priority from Colombian application serial number NC2016/0004700 filed on Nov. 28, 2016, and from Colombian application Ser. No. NC2016/0004900 filed on Dec. 1, 2016, which are incorporated herein by reference in its entirety.

BACKGROUND

Field of the Invention

The organ-chimerization maintenance apparatus described herein relates to the field of conservation of biological organisms. More specifically to an apparatus for the maintenance of live organs used in regenerative medicine.

Background of the Prior Art

Devices to assist in transplantation of live organs for organ transplants are well-known in the art. For example, the ex vivo lung perfusion (EVLP) technique has emerged as a technique for assessment, resuscitation, and possible repair of organs from donors. This is a field in rapid development with important clinical implications.

Particularly, it centers on human and animal experience, different perfusion-ventilation strategies, and the impact of different perfusions; EVLP is a potential research tool. This will provide information on EVLP and its future development in the clinical field of lung transplants.

Lung transplant seek to save the lives of patients with terminal lung disease. However, the number of patients waiting for a lung transplant is much higher than the number of available donors. On average, only 15% of the lungs from multi-organ donors are used for transplant; the rest are considered inadequate due to pulmonary lesions that occur after brain death and complications associated to treatment in intensive care unit (ICU) (for example, barotrauma and pulmonary edema). One of the concerns in organ transplantation relate to rejection of the transplanted organ due to genetic incompatibility between the host and the donor. There is a need for procedures that reduce the risk of organ rejection.

SUMMARY

An organ-chimerization maintenance device is described. The device comprises at least one large cannula connector that connects to at least one of the organ's vessels. The large cannula is configured to supply a chimerization solution to the organ. The device further comprises an oxygenation cannula connector. In some embodiments, the device comprises a container with a support plate, an adjustable perforated plate, at least one cannula connector, and an oxygenation cannula connector, wherein the support plate and the container form an enclosure that facilitates organ chimerization. In other embodiments, the support plate comprises a plurality cannula connectors. In other embodiments, the device also includes a recirculation cannula connector. The organ-chimerization maintenance device may also comprise a diffuser connected to the oxygen cannula connector.

In one embodiment, the organ-chimerization maintenance device also includes a basket. The basket includes a door and a base support. In some embodiments, the basket has a handle. The basket may also include a door with a latch. In some embodiments, the support plate has handles. The organ-chimerization maintenance device may also comprise a seal. In some embodiments, the organ-chimerization maintenance device container is made of glass and the seal is made of silicon.

BRIEF DESCRIPTION OF THE DRAWINGS

To complement the description and to help to understand better the technical characteristics of the invention, a set of figures accompany the present specification as an integral part thereof; these are defined thus:

FIG. 7 is an isometric view of the basket in the open position.

DETAILED DESCRIPTION

The present device serves as a mechanical means for organ chimerization prior to transplantation. Chimerization in this context refers to a process for the fusion of stem cells from a receptor and a donor, which will result in a reduction of rejection by the receptor because the transplanted organ is not recognized as foreign by the receptor's immune system.

Figure 1:
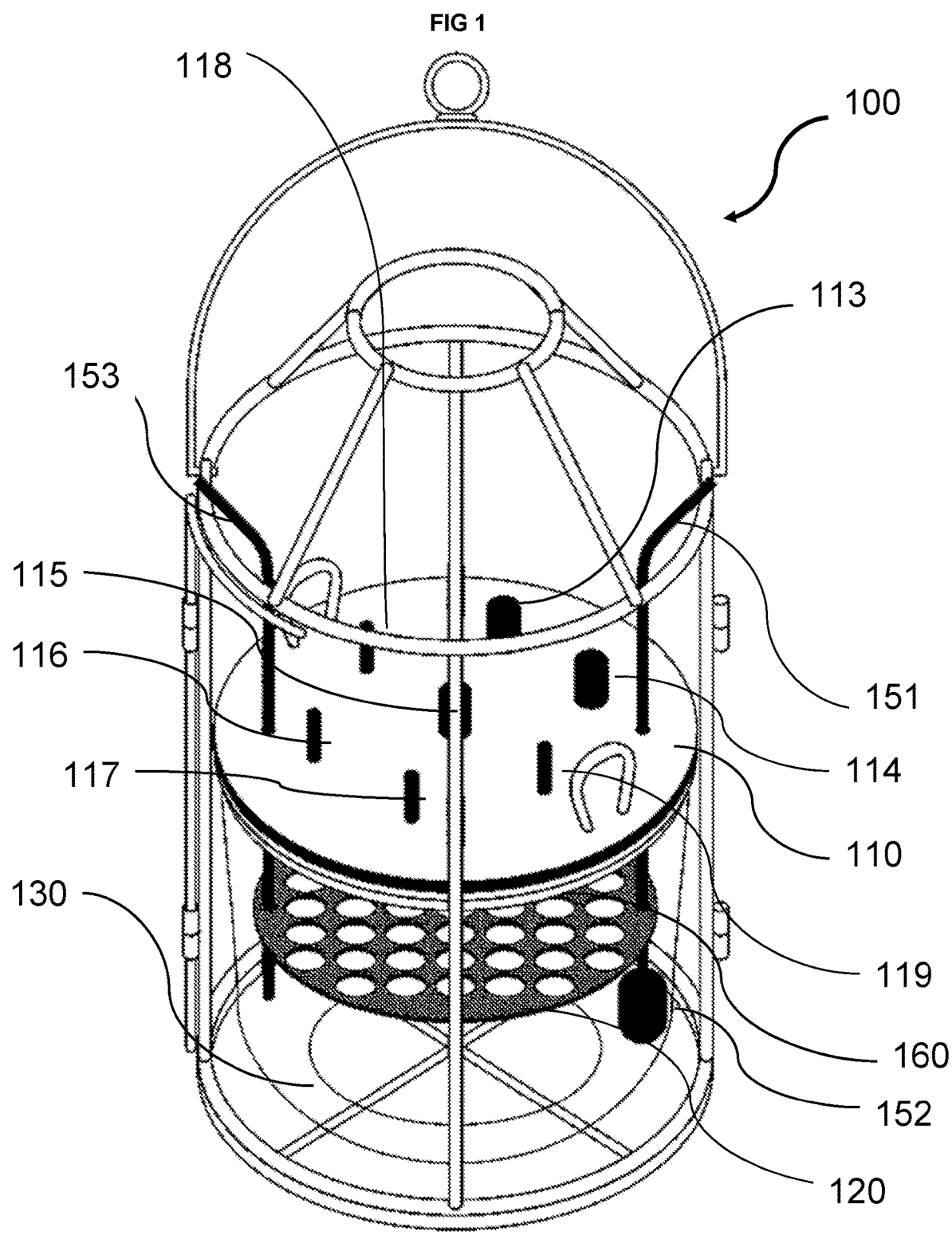
FIG. 1 is an isometric view of the organ-chimerization maintenance device

As shown FIG. 1, one embodiment of the organ-chimerization maintenance device 100 comprises a container 130 and a support plate 110. The support plate 110 sits on the top of the container 130 forming a sealed enclosure for the organ to be put through chimerization. The container 130 includes an adjustable perforated plate 120. The adjustable perforated plate 120 is used to hold the organ in place and the adjustable perforated plate 120 can be adjusted to ensure the organ can be placed within the enclosure.

The support plate 110 has at least one cannula connector 113, 114, 115, 116 117, 118, 119. It is contemplated that, in one embodiment, the device 100 may include a plurality of cannula connectors 113, 114, 115, 116, 117, 118, 119. The size of the cannula connectors 113, 114, 115, 116, 117, 118, 119 varies depending on the function to be performed. In one embodiment, there are large cannula connectors 113, 114, 115 and small cannula connectors 116, 117, 118, 119. In some embodiments there is one large cannula connector 113, 114, 115. The large cannula connectors 113, 114, 115 provide a means to connect to the organs vessels. For example, the large cannula connectors 113, 114, 115 can connect to the organ's aortic or arterial vessels, large and medium size veins. The large cannula connectors 113, 114, 115 in some embodiments are designed to fit large and small respiratory ducts, such as bronchi in the lungs. It is contemplated that the large cannula connectors 113, 114, 115 may have different sizes to enable the functions discussed and connections to the organ being transplanted. In some embodiments, the large cannula connectors 113, 114, 115 are used to supply a chimerization solution to the organ or the device 100. The small cannula connectors 116, 117, 118, 119 are designed for various probes to monitor the organ being transplanted and the contents of the container. In some embodiments, the small cannula connectors 116, 117, 118, 119 accept various probes such as pH, gases, electrolytes and temperature, osmolality meters, and others as needed. It is understood that other types of probes may be utilized.

Figure 2:
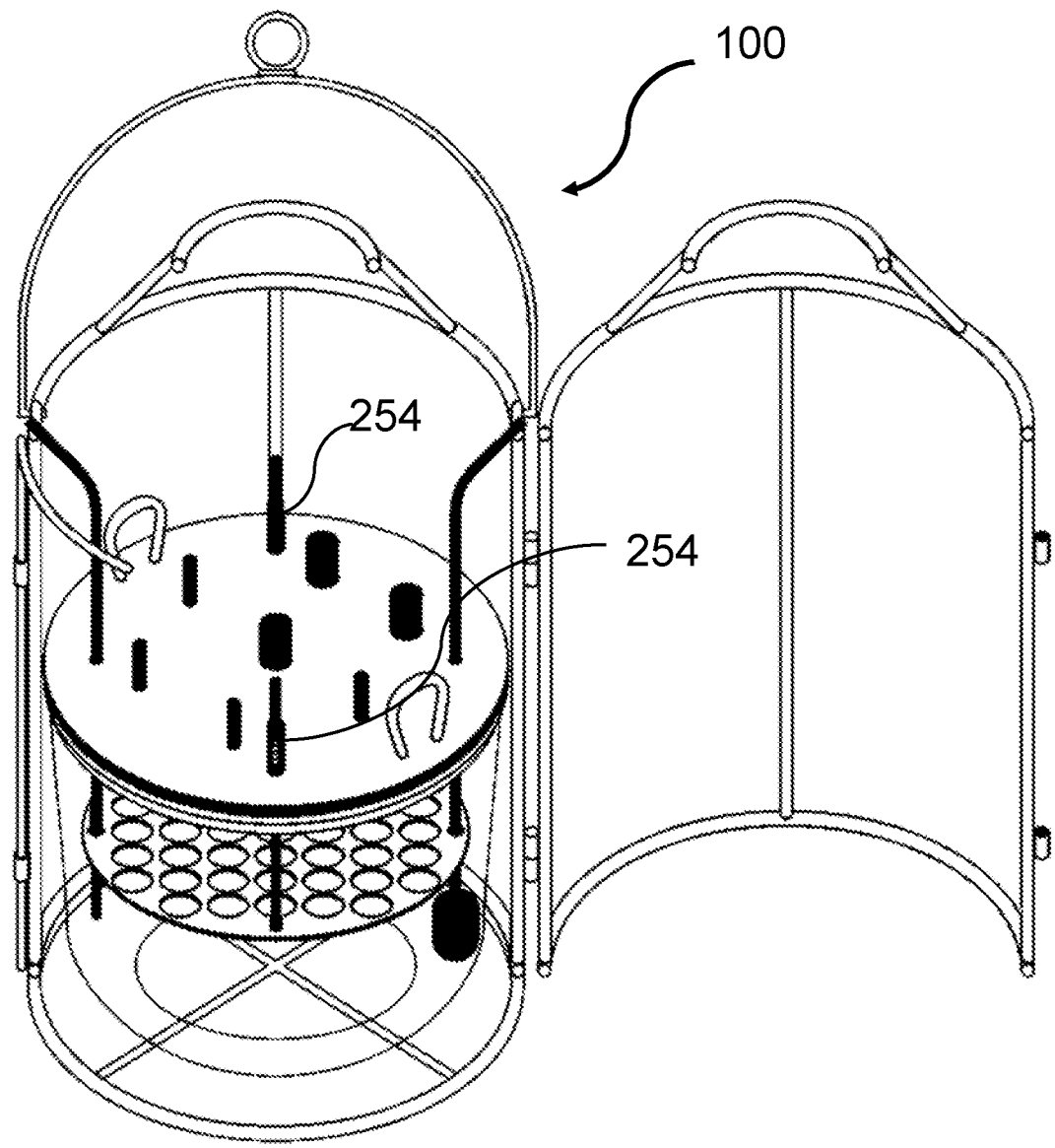
FIG. 2 is an isometric view of the organ-chimerization maintenance device with basket in open position.
Figure 3:
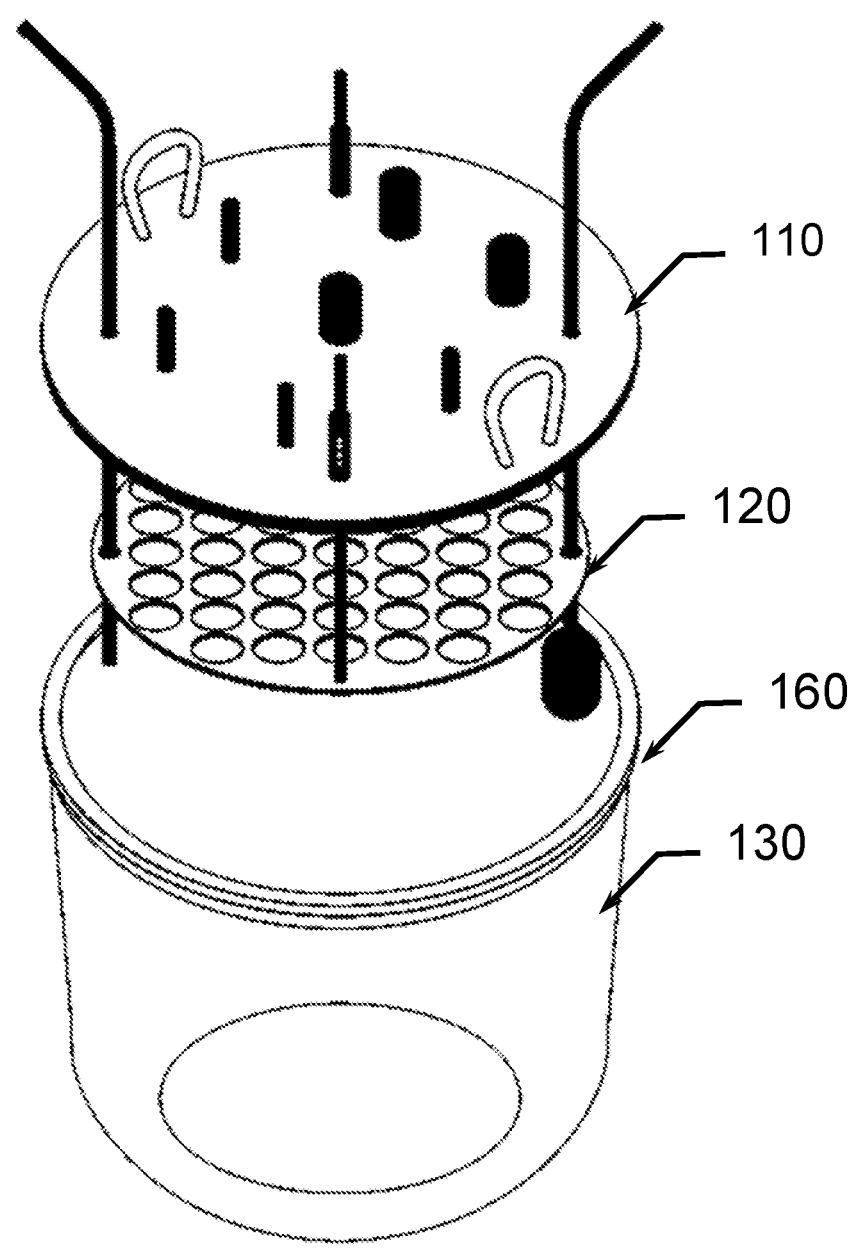
FIG. 3 is an isometric blown up view of the interior of the device.
Figure 4:
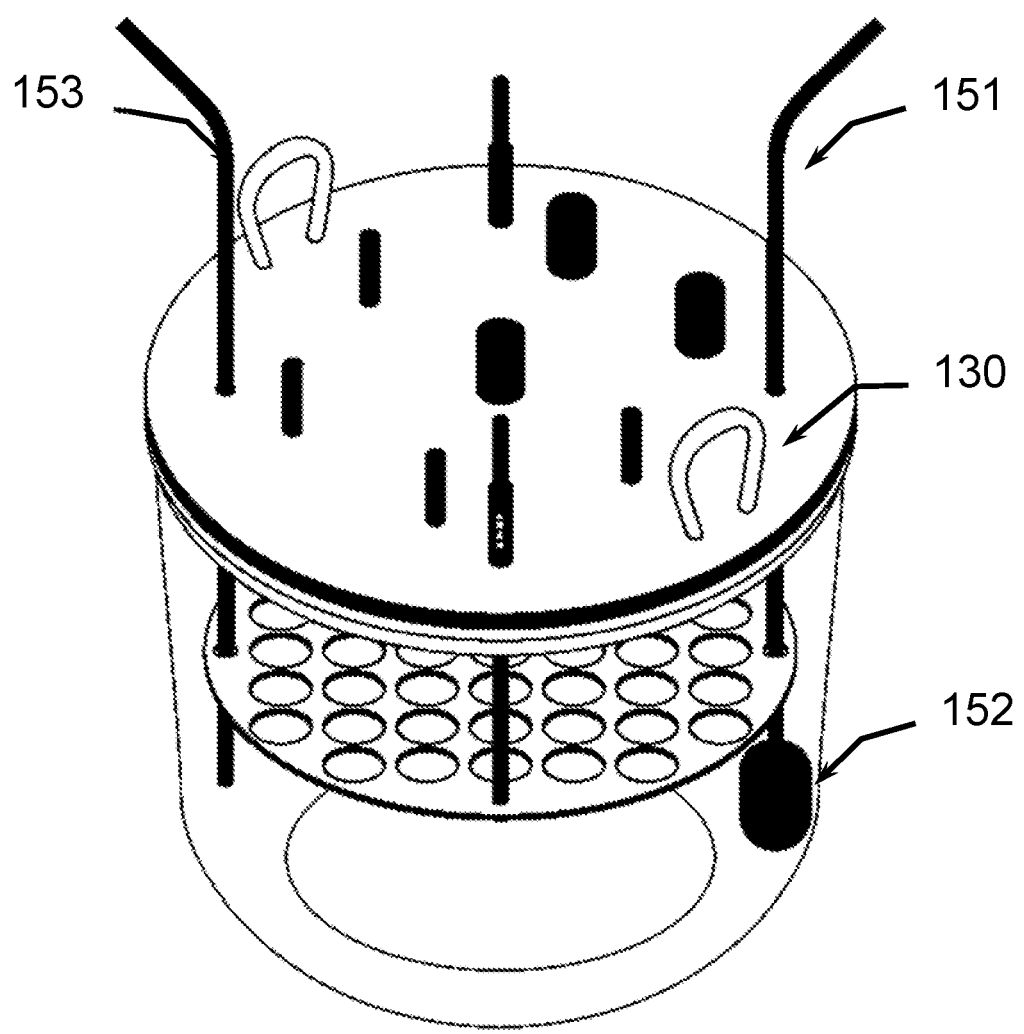
FIG. 4 is and isometric assembly view of the interior of the device.

The support plate 110 sits on a seal 160 coupled to the container 130. The support plate 110 and the seal 160 on the support plate 110 once closed prevent any external contaminants to enter the inside of the container 130. FIGS. 2 and 3 show the components of one embodiment in two configurations. In FIG. 2 the support plate 110 and perforated plate 120 components are removed from the container 130. In FIG. 2 the support plate 110 and perforated plate 120 are secured to the container 130. The support plate 110 has one or more cannula connections 113, 114, 115, 116, 117, 118 119, and oxygenation cannula connector 151, and a recirculation cannula connector 153.

In one embodiment, the device is configured as described below to maintain the organ alive. Once a rescue team obtains the organ, the organ is placed on the support plate in between the support plate 110 and the perforated plate 120. The principal artery of the organ is connected to a line from a peristaltic pump (not shown) through a first large cannula connector 113, the organ is connected to a ventilator (not shown), if necessary, through a second large cannula connector 114, the third large cannula connector 115 in some embodiments is used for evacuation and replacement of the culture medium and placement of mesenchymal stem cells. The large cannula connector 115 may include a stopper (not shown) to prevent the contents of the container from being released. In yet a further embodiment, catheters are introduced through the small cannula connectors 116, 117, 118, 119 to measure pH, temperature, gases (pO2, pCO2), or take samples from the culture medium. Each cannula connector may contain rubber stoppers or other types of plugs that allow the various elements to be introduced without allowing the contents of the container to be released. The stoppers also maintain the aseptic nature of the container preventing contamination of the organ being maintained in the container.

The oxygenation cannula 151 is connected to an oxygen source (not shown), to maintain the hyperoxia state. The oxygen cannula 151, in some embodiments, includes a diffuser 152. The recirculation cannula connector 153 collects medium toward the peristaltic pump (not shown) to complete the circuit.

The space between the support plate 110 and the perforated plate 120 of the organ-chimerization maintenance device 100 can be adjusted to permit maintaining the organ immersed in the culture medium in the container 130, besides serving as a guide and support for large vessels to avoid damage during their manipulation. In one embodiment, the space between the support plate 110 and the perforated plate 120 is adjusted by an adjustment bar 254 that links the support plate 110 and the perforated plate 120. In some embodiments, multiple adjustment bars 254 connect the support plate 110 and the perforated plate 120. It is contemplated that a person of ordinary skill in the art may utilize any other means to adjust the distance between the support plate 110 and the perforated plate 120.

The container 130 has a seal 160 that isolates the organ from the environment. The seal 160 is located on the top edge of the container 130 and seals the container when the support plate 120 is place on the container 160. The container 130 is made from any material that isolates the organ from the environment and is biomedically acceptable. The materials include glass, ceramic, or any other material that is inert to the organ's culture medium. The seal 160 is made from a material that provides among plastic, silicon, or any other material suitable for conservation of the medium and the organ.

Figure 5:
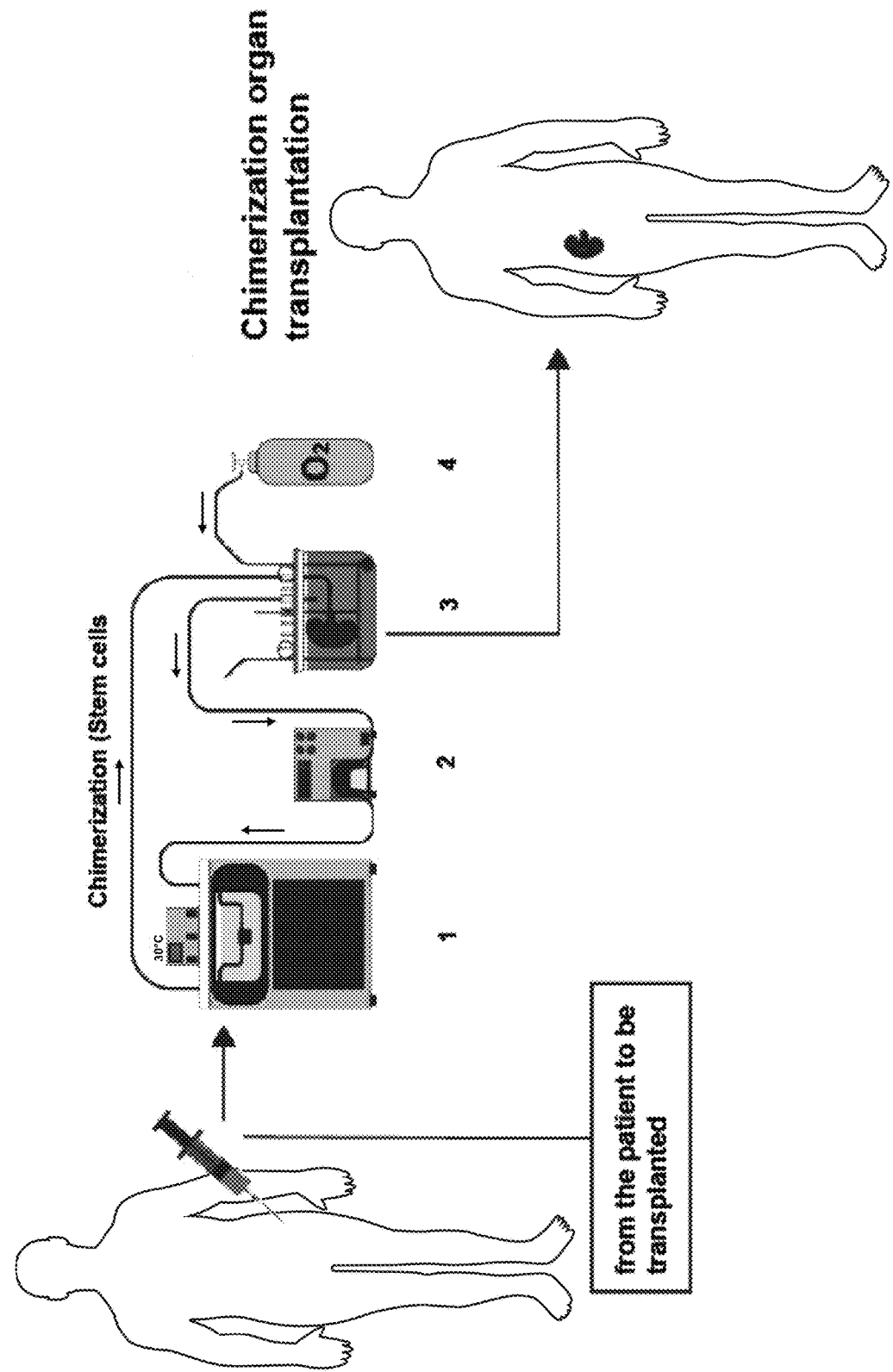
FIG. 5 is a graphical representation of a system that comprises the device.

As shown in FIG. 5, the device 100 is used in a system for the chimerization of organs to be transplanted. The organ stored in the container 130 in some embodiments is attached to a heater/cooler 1 through the one of the large cannulas 113. The heater cooler is, in turn, connected to a peristaltic pump 2. The peristaltic pump is connected to the recirculation cannula connector 153. The oxygen cannula 151 is connected to an oxygen source. It is contemplated that other gases may be introduced through the oxygen cannula 151 as may be necessary. The device 100 provides recirculation of a chimerization solution and oxygenacion of the organ during the chimerization process. The connections to the various parts of the system can be removed and the device 100 can be utilized to transport the organ from the donor site to the recipient's site. In some instances the donor may be in the same location as the recipient. In other instances, the donor may be in a different institution or hospital and the device 100 can be utilized to transport the organ over short or long distances.

Figure 6:
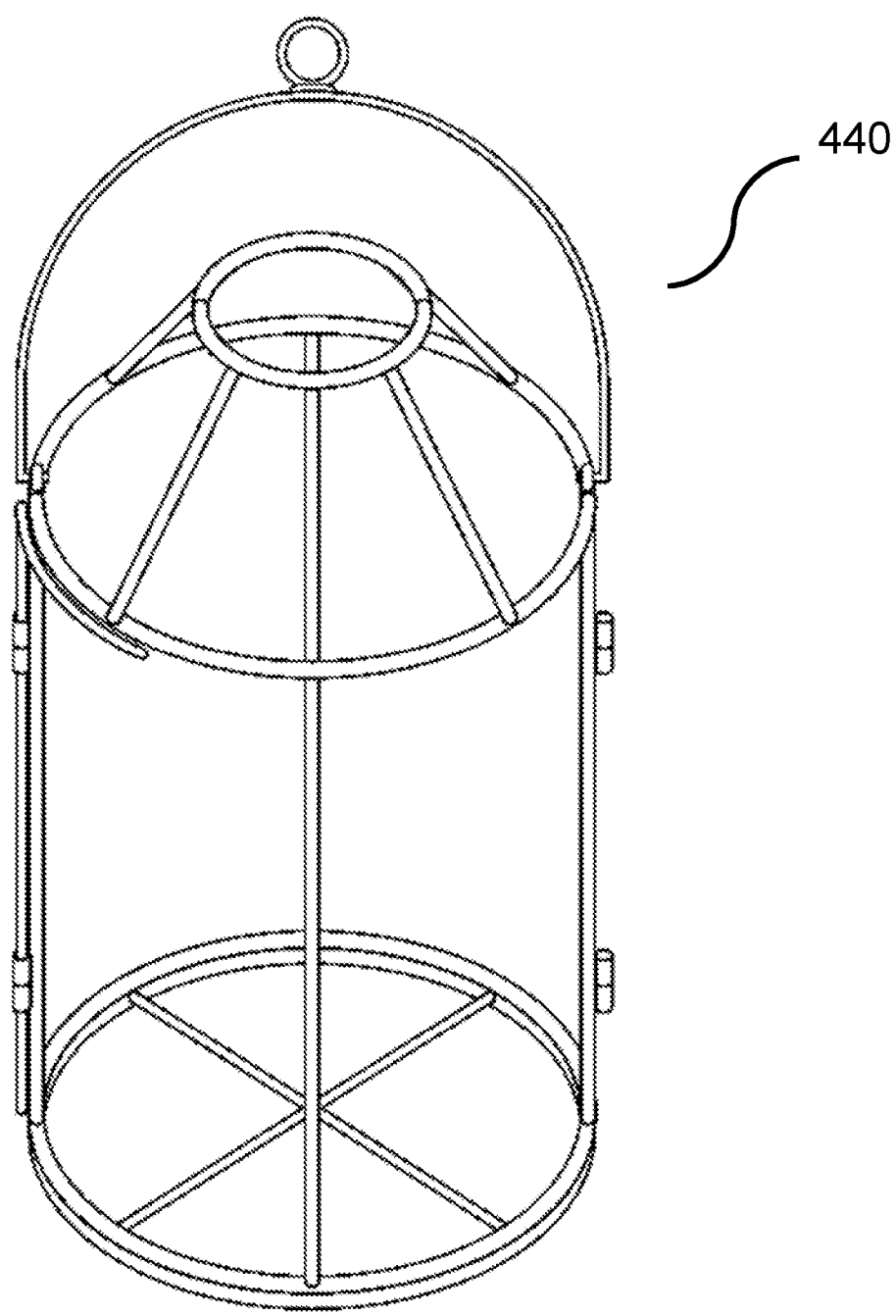
FIG. 6 is an isometric view of a basket.

The basket 440 is described in detail in FIGS. 6 and 7. The basked 440 has a moving door 441 through which the container 130 is place inside the basket 440. The basket 440 is designed to protect the container 130 and any organ being stored therein. The basket 440 is made up of a basket base support 442 and a door 441 joined by hinges 444. The basket has a closing mechanism 443. In some embodiments, the closing mechanism 443 is a latch or a closing lever 446. The basket 440 also has a grip handle 445.

In some embodiments, the support plate 110 and perforated plate 120 and their connections are made of materials selected among stainless steel, thermo-plastic materials, and thermos-stable materials suitable for conservation of the medium and of the organ. Such materials are biocompatible and of appropriate medical grades. Similarly, the basket 440 in some embodiments is manufactured of materials selected from stainless steel, thermos-plastic materials, and thermo-stable materials suitable for the resistance necessary to support the device altogether.

The prior description can only be taken as reference and not limiting in its components or its explicit relation; rather, it has been described to provide a clear idea on the general conformation of the matter of the invention claimed.

What is claimed is:

1. An organ-chimerization maintenance device, comprising:
    a transportable organ container configured to contain an organ;
    at least one cannula connector configured to connect to at least one of the organ's vessels and to supply a chimerization solution to the organ;
    a support plate, the support plate comprising a plurality of cannula connectors disposed throughout the support plate;
    an adjustable perforated plate disposed below the support plate and configured to support the organ on an upper surface thereof;
    wherein the adjustable perforated plate is attached to the support plate by an adjustment bar, wherein the adjustment bar is configured to adjust a distance between the support plate and the perforated plate and configured to secure said organ placed within the transportable organ container; and an oxygenation cannula connector extending through the support plate and adjustable perforated plate, and includes a diffuser disposed within the transportable organ container and connected to a lower end of said oxygenation cannula connector, and wherein the plurality of cannula connectors include the at least one cannula connector and the oxygenation cannula connector.

2. The organ-chimerization maintenance device of claim 1, wherein said plurality of cannula connectors include a recirculation cannula connector.

3. The organ-chimerization maintenance device of claim 1, further comprising a basket.

4. The organ-chimerization maintenance device of claim 3, wherein the basket comprises a door and base support.

5. The organ-chimerization maintenance device of claim 3, wherein the basket has a handle.

6. The organ-chimerization maintenance device of claim 3, wherein the basket has a door with a latch.

7. The organ-chimerization maintenance device of claim 1, wherein the support plate has handles.

8. The organ-chimerization maintenance device of claim 1, further comprising a seal.

9. The organ-chimerization maintenance device of claim 8, wherein the transportable organ container is made of glass and the seal is made of silicon.

* * * * *